(12) United States Patent
Salzman

(10) Patent No.: US 8,535,276 B2
(45) Date of Patent: *Sep. 17, 2013

(54) SYRINGE-ATTACHED TOPICAL ANESTHETIC DISPENSER

(75) Inventor: Marc J. Salzman, Louisville, KY (US)

(73) Assignee: BellaNovus Development Company LLC

( * ) Notice: Subject to any disclaimer, the term of this patent is extended or adjusted under 35 U.S.C. 154(b) by 311 days.

This patent is subject to a terminal disclaimer.

(21) Appl. No.: 12/585,909

(22) Filed: Sep. 29, 2009

(65) Prior Publication Data

US 2010/0022965 A1    Jan. 28, 2010

Related U.S. Application Data

(63) Continuation-in-part of application No. 12/213,892, filed on Jun. 26, 2008.

(51) Int. Cl.
*A61M 5/00* (2006.01)
*A61M 5/315* (2006.01)
*A61M 35/00* (2006.01)

(52) U.S. Cl.
USPC ........... 604/191; 604/112; 604/181; 604/187; 604/218; 604/236; 604/289; 604/310; 604/311

(58) Field of Classification Search
USPC .................. 604/112, 181, 187, 191, 218, 232, 604/236, 289, 310, 311, 173, 257, 258
See application file for complete search history.

(56) References Cited

U.S. PATENT DOCUMENTS

| | | | |
|---|---|---|---|
| 3,605,742 A | 9/1971 | Tibbs | |
| 4,226,235 A * | 10/1980 | Sarnoff et al. | 604/136 |
| 4,725,265 A | 2/1988 | Sairenji | |
| 4,931,040 A * | 6/1990 | Haber et al. | 604/110 |
| 5,236,419 A | 8/1993 | Seney | |
| 5,341,993 A * | 8/1994 | Haber et al. | 239/331 |
| 6,312,412 B1 * | 11/2001 | Saied et al. | 604/191 |
| 6,936,028 B2 | 8/2005 | Hommann et al. | |
| 2005/0054991 A1 * | 3/2005 | Tobyn et al. | 604/290 |

* cited by examiner

*Primary Examiner* — Kevin C Sirmons
*Assistant Examiner* — Shefali Patel
(74) *Attorney, Agent, or Firm* — H. Jay Spiegel

(57) ABSTRACT

A topical anesthetic dispenser is releasably attachable to a pre-filled disposable syringe. A pair of clips receive a barrel of the syringe. The clips are on a housing receiving a pre-filled cannister of a topical numbing agent and including a chamber. The cannister includes an aerosol dispensing valve actuated by a button which when pressed moves the cannister with respect to an actuator for the valve.

12 Claims, 8 Drawing Sheets

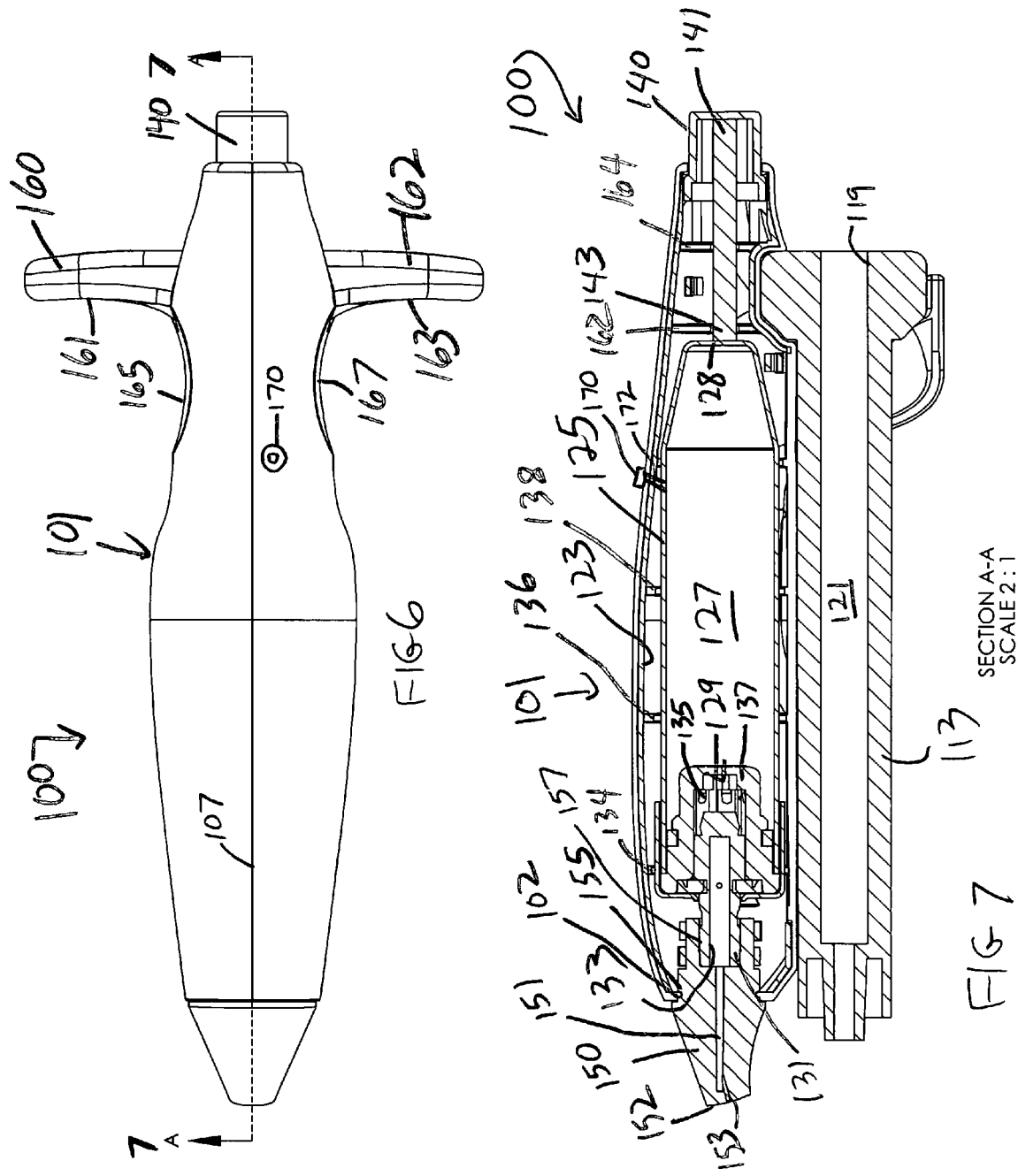

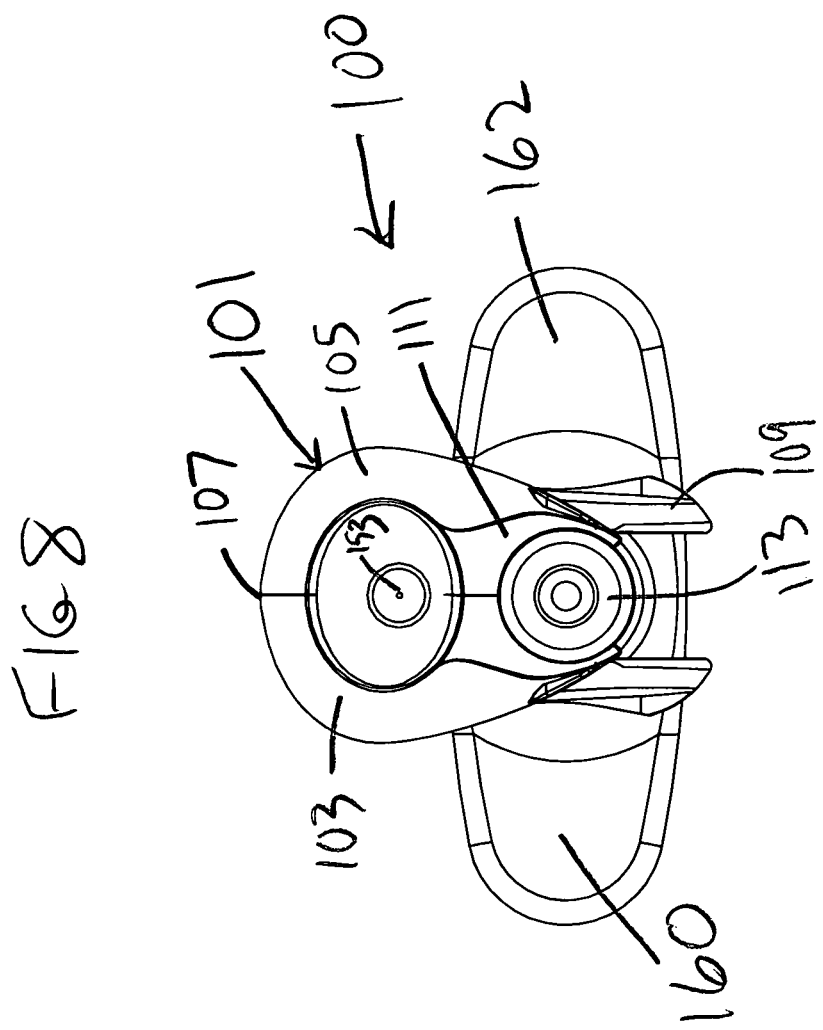

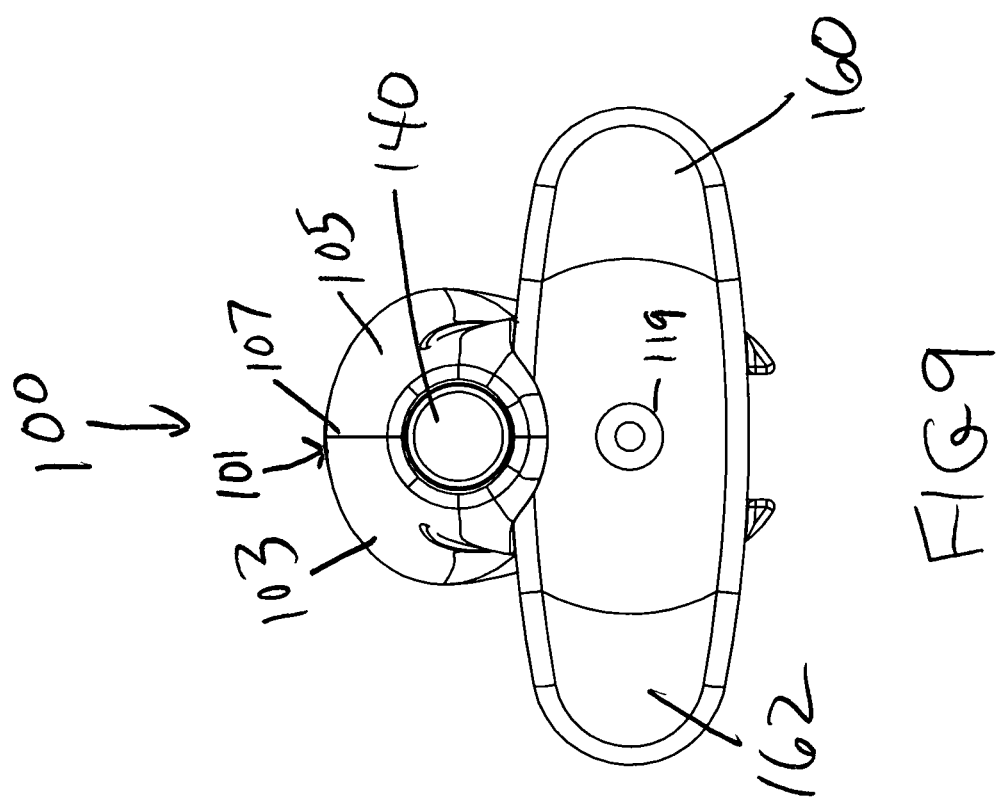

SYRINGE-ATTACHED TOPICAL ANESTHETIC DISPENSER

This application is a Continuation-in-Part of application Ser. No. 12/213,892, filed Jun. 26, 2008.

BACKGROUND OF THE INVENTION

The present invention relates to embodiments of a syringe-attached topical anesthetic dispenser. Syringes are employed millions of times daily all over the world to inject medicines into people as well as animals. Many times, injections are made in areas of the body that are somewhat less sensitive to pain. Other locations of the body where injections are contemplated are significantly more sensitive to pain and the patient feels a pinching sensation that may be quite painful as the syringe needle is inserted beneath the skin. Such areas include, for example, areas of the face such as the forehead as well as the lips.

Use of cosmetic injections into the face of a patient has become more and more common. Thus, for example, a chemical known by the Trademark BOTOX® is often injected into the face, particularly into a patient's forehead, to paralyze the subcutaneous muscles and temporarily eliminate visible wrinkles in the forehead. Such injections typically last several months at most and must be repeated over and over again, periodically, to maintain the non-wrinkled appearance.

Similarly, filler materials are often used, for example, within a patient's lips, to expand their size in keeping with the desires of the patient. Such dermal fillers include those sold under the Trademarks JUVEDERM®, RESTYLANE® and RADIESSE®.

When such chemicals are injected, typically to reduce pain associated with such injections, two options are employed. A first option is the use of a topical numbing cream applied to the area where the injection will take place. Typically, topical numbing creams require 40 minutes to 1 hour with occlusion to successfully numb the skin to a sufficient degree to render the subsequent injections painless. The second technique involves the use of numbing medicines such as LIDOCAINE®. However, the use of numbing medicines such as LIDOCAINE® is less preferred because it also requires needle injection through the skin which is not only painful, but can also distort the surrounding area, thereby making determination of the amount of filler to be subsequently placed more difficult. Additionally, injection of LIDOCAINE® may dilute the particles of subsequently injected BOTOX® making it easier for the BOTOX® substance to travel to distant locations and paralyze muscles the patient did not want to have paralyzed.

Additional methods of pre-injection cooling of the skin and associated tissues are also employed. For example, plain ice or ice-packed devices may be placed onto the skin and held there for a short period of time to numb the skin. Use of ice or ice-packed devices is inefficient and initially painful for the patient. Such devices must be placed onto the skin and held there for a short time and then must be removed with one hand and moved away from the patient by passing to an assistant or using some other technique. When these techniques are employed, often the physician is holding the ice pack which causes the physician's hand to be cooled and reduces effectiveness of the use of that hand. When the physician is injecting cosmetic medicines, one hand is used to work the syringe and the other is used to tense the skin, that is, to move the skin away from the muscle or palpate a bony landmark to aid in locating the proper place to inject the medicine. Use of ice can be messy and cold water resulting from melting of the ice can drip over the area to be injected. Use of ice, whether exposed or packed, limits the effectiveness of the physician who needs to have both hands available for the injection as explained above.

Another way to cool the area of the injection is to use a device consisting of a hose attached to an air cooling machine that blows cold air at the face. One such device is known by the Trademark SMARTCOOL®. Such devices are expensive and often the patient complains that, as the cold air is blown at the face, it takes their breath away as quickly moving air rushes by their nose. Additionally, the surface area cooled by a SMARTCOOL® device is often significantly greater than necessary to numb an anticipated injection.

Each of these prior art techniques used preliminary to an injection in a sensitive area of a patient such as on the face has its problems as explained above. The present invention was developed, keeping these problems in mind, and in an effort to provide a new technique to prepare a sensitive area of the human body to receive a cosmetic injection while avoiding messiness, pain, inconvenience, and expense. It is with these thoughts in mind that the present invention was developed.

Applicant is aware of the following prior art references:

U.S. Pat. No. 3,605,742 to Tibbs teaches a painless injection device which includes means for spraying a cooling fluid onto an injection site to numb the area prior to injection. The Tibbs device is extremely cumbersome including a large housing enclosing a syringe as well as the numbing device. An additional problem with Tibbs is that the needle path is not visible until the mechanism latch is released to expose the syringe bottom and attached needle. The actual depth of penetration of the needle appears to be set by the action of a spring which is not a sufficiently precise enough structure to allow placement of substances such as BOTOX® medicament or subcutaneous fillers. Additionally, the Tibbs device is clumsy since it has one depressor mechanism to express the syringe from the housing using a spring device and then a further attachment to the plunger end to deliver the medicament into the tissues. This may lead to imprecise placement of either the needle tip location or the desired depth of medicament dispersal, or both.

U.S. Pat. No. 4,725,265 to Sairenji discloses a syringe having an attached cooling gas injection nozzle for injecting a cooling gas onto skin where an injection is to take place. The gas is a vapo-coolant and the device includes a retractable rigid nozzle that is spring activated and serves as a conduit for spraying the vapo-coolant. The spring activation of the Sairenji device requires a second hand to disengage the downward position of the nozzle. Furthermore, Sairenji discloses a chamber into which the desired medicament is filled for injection into the patient, rather than a pre-filled disposable syringe. The Sairenji device is not practical for use where multiple sequential injections in spaced locations are contemplated. This is because all of the actions necessary to cause dispensing of the vapo-coolant then the injection make the Sairenji device extremely cumbersome and complicated.

U.S. Pat. No. 5,236,419 to Seney discloses a syringe including a distal portion containing a freezable chemical designed to engage the surface of the skin where an injection is to take place to cool that portion of the skin. Seney also discloses that it is known in the prior art to spray ethyl chloride onto a location of the skin as a topical anesthetic. However, Seney fails to teach or suggest dispensing a topical anesthetic by a device attached to a disposable syringe in the manner contemplated by the present invention.

U.S. Pat. No. 6,312,412 to Saied et al. discloses an apparatus and method for painless intramuscular or subcutaneous injections. In the Saied et al. device, a numbing agent is injected subcutaneously using a needle. The present invention improves upon the Saied et al. device by providing a topical dispensing of a numbing agent so that the pain inflicted on the patient by injecting the numbing agent is completely eliminated.

U.S. Pat. No. 6,936,028 to Hommann et al. discloses a cooling device for an injection apparatus. The Hommann et al. device is somewhat similar to that of Seney as including a cooling element surrounding the location where the syringe will be inserted, which cooling element is placed on the skin to cool it and numb it prior to the injection.

The present invention improves upon the teachings of the prior art described above by providing a simple spraying mechanism for spraying a topical anesthetic onto the skin where an injection is to take place using a disposable and sometimes pre-filled syringe.

SUMMARY OF THE INVENTION

The present invention relates to embodiments of a syringe-attached topical anesthetic dispenser. The present invention includes the following interrelated objects, aspects and features:

(1) In a first aspect, the present invention in its preferred intended use is intended to be releasably attachable to a pre-filled disposable syringe. Of course, if desired, the syringe may be initially empty and require filling prior to injection.

(2) In a first embodiment, a clip is provided that includes a first opening sized to receive the barrel of the syringe. That opening may be formed in a clip portion that is resilient and includes a longitudinally open slot allowing the syringe barrel to be inserted laterally into the opening. Alternatively, the syringe barrel may also be inserted into the opening of the clip portion longitudinally. In either case, it is preferred that the longitudinally extending opening in the clip portion has a width less than the diameter of the barrel of the syringe so that if the syringe is being attached to the clip portion through lateral movement, the flexibility of the clip portion allows the longitudinal opening to be temporarily enlarged until the largest diameter portion of the syringe barrel passes the opening, whereupon the resiliency of the clip portion causes it to spring back and retain the syringe barrel within its opening.

(3) In the first embodiment of the present invention, the clip includes a receptacle portion sized to closely receive a pre-filled canister of a topical numbing agent such as, for example, ethyl chloride. Typically, the pre-filled canister includes a generally cylindrical chamber portion receivable within the receptacle portion of the clip and a distal neck portion having an outlet that may be opened by piercing a disc-like closure, thereby allowing the contents of the canister to be dispensed.

(4) A dispenser is attached to the distal neck portion of the canister. In the first embodiment, the dispenser includes an elongated flexible tube attached to the distal neck portion of the canister and surrounded by a rigid tube for at least a portion of its length. A pivotable lever carries a tube compressor including a pinching member extending through an opening in the rigid tube and spring biased to a position at which it pinches closed the elongated passageway through the flexible tube. The elongated actuating lever is spring biased to a position at which the flexible tube is pinched closed.

(5) Preferably, the flexible tube protrudes distally of the rigid tube and is made of a suitable material allowing the distal end of the flexible tube to be bent and configured to aim the topical anesthetic at a desired location on the skin of the user. If desired, a nozzle may be provided at the distal end of the flexible tube designed to cause the topical anesthetic to be sprayed in a desired spray pattern.

(6) In a second embodiment of the present invention, a pair of clips releasably receive the barrel of a hypodermic syringe. The clips are attached to an elongated housing including a chamber sized to receive a canister of a topical anesthetic.

(7) The housing is preferably formed by two halves defining a longitudinal split therebetween so that they are assembled together along the split to create the chamber receiving the canister. The canister preferably is of the aerosol type and includes an actuator for actuating an internal valve and consisting of an elongated tube having an axis of elongation along which an outlet passageway is formed. When the actuator is pushed into the canister, the valve is opened allowing release of the topical anesthetic within the canister.

(8) In the second embodiment, a nozzle is fluidly connected to the actuator of the canister in such a way that the nozzle has a bore therethrough aligned with the passageway through the canister valve actuator so that when the canister valve is opened, topical anesthetic may flow through the outlet passageway in the actuator, and thence through the passageway in the nozzle to a reduced diameter outlet nozzle.

(9) At the end of the housing remote from the nozzle, an actuator button is provided that includes a stem engaging the closed end of the canister. When the button is depressed, the canister is caused to move in the same direction as the actuator stem. With the nozzle fixed in the housing, this movement causes the canister to move with respect to its actuator, thereby opening the valve and causing dispensing of the topical anesthetic from within the canister through the nozzle and its outlet bore. When the button is released, the restoring force of a spring incorporated in the canister valve closes the valve and restores the actuator button to its previous un-actuated position. If desired, a cam device may be associated with the actuator button so that a prescribed metered dose of topical anesthetic is dispensed each time the button is pushed, regardless of how long it is held in the depressed position.

(10) The clip closest to the proximal end of the syringe has incorporated therewith a pair of opposed wing-like appendages sized and configured to be engaged by fingers of the user, with the user's thumb being employed to depress the actuator button.

(11) The second embodiment of the present invention is intended, in one variation, to be used until the canister is depleted of topical anesthetic and then discarded. For this purpose, in assembly of the second embodiment, the two longitudinally split halves of the housing are assembled about the nozzle, the canister, and the actuator button with its actuator stem. Adjoining edges of the housing halves are adhered together by a suitable adhesive and are preferably sealed using an ultraviolet activated sealant. Prior to adhering the housing halves together, the nozzle is fitted over the tubular actuator for the canister in an interference fit. In another variation, a fill port is provided on the device to facilitate refilling the canister.

(12) The present invention in each of its embodiments is easily attached to a disposable syringe and may be easily removed therefrom when the disposable syringe is to be discarded. Since the inventive topical anesthetic dispenser never comes in contact with the patient and its design precludes contamination of the flexible tube in the first embodiment, the housing in the second embodiment, and the canister containing the topical anesthetic, the inventive device may be used multiple times with multiple syringes and, even, multiple patients. Of course, the device may be used solely with a single patient and discarded after such use.

As such, it is a first object of the present invention to provide a syringe-attached topical anesthetic dispenser.

It is a further object of the present invention to provide such a device in which a disposable syringe may have the dispenser attached thereto and easily removed therefrom when the syringe is to be discarded.

It is a still further object of the present invention to provide such a device in which in a first embodiment, a flexible tube dispenses a topical anesthetic and the flexible tube may be bent to aim the anesthetic at a desired location on the skin of a patient.

It is a yet further object of the present invention to provide such a device in which in a first embodiment, a tube compressor is employed to control dispensing of the topical anesthetic.

It is a yet further object of the present invention to provide such a device in which in the first embodiment, the tube compressor is biased to a position stopping flow of topical anesthetic and includes an actuating lever that may be pivoted to control flow of topical anesthetic.

It is a yet further object of the present invention to provide such a device in a second embodiment thereof in which an aerosol canister is provided having an actuator consisting of an elongated tube incorporated into an aerosol valve.

It is a yet further object of the present invention to provide such a device in a second embodiment thereof in which the nozzle consists of an elongated passageway in a hard molded member, and the canister is actuated by depressing an actuator button that moves the canister with respect to the nozzle and the canister actuator.

It is a still further object of the present invention to provide such a device in a second embodiment thereof in which wing-like appendages are provided to allow engagement by the fingers of the user while the thumb is used to depress the actuator button.

These and other objects, aspects and features of the present invention will be better understood from the following detailed description of the preferred embodiment when read in conjunction with the appended drawing figures.

BRIEF DESCRIPTION OF THE DRAWINGS

FIG. 6 shows a top view of the second embodiment of the present invention.

FIG. 7 shows a cross-sectional view along the line 7-7 of FIG. 6.

FIG. 8 shows a front view of the second embodiment of the present invention.

FIG. 9 shows a rear view of the second embodiment of the present invention.

SPECIFIC DESCRIPTION OF THE PREFERRED EMBODIMENTS

Figure 1:
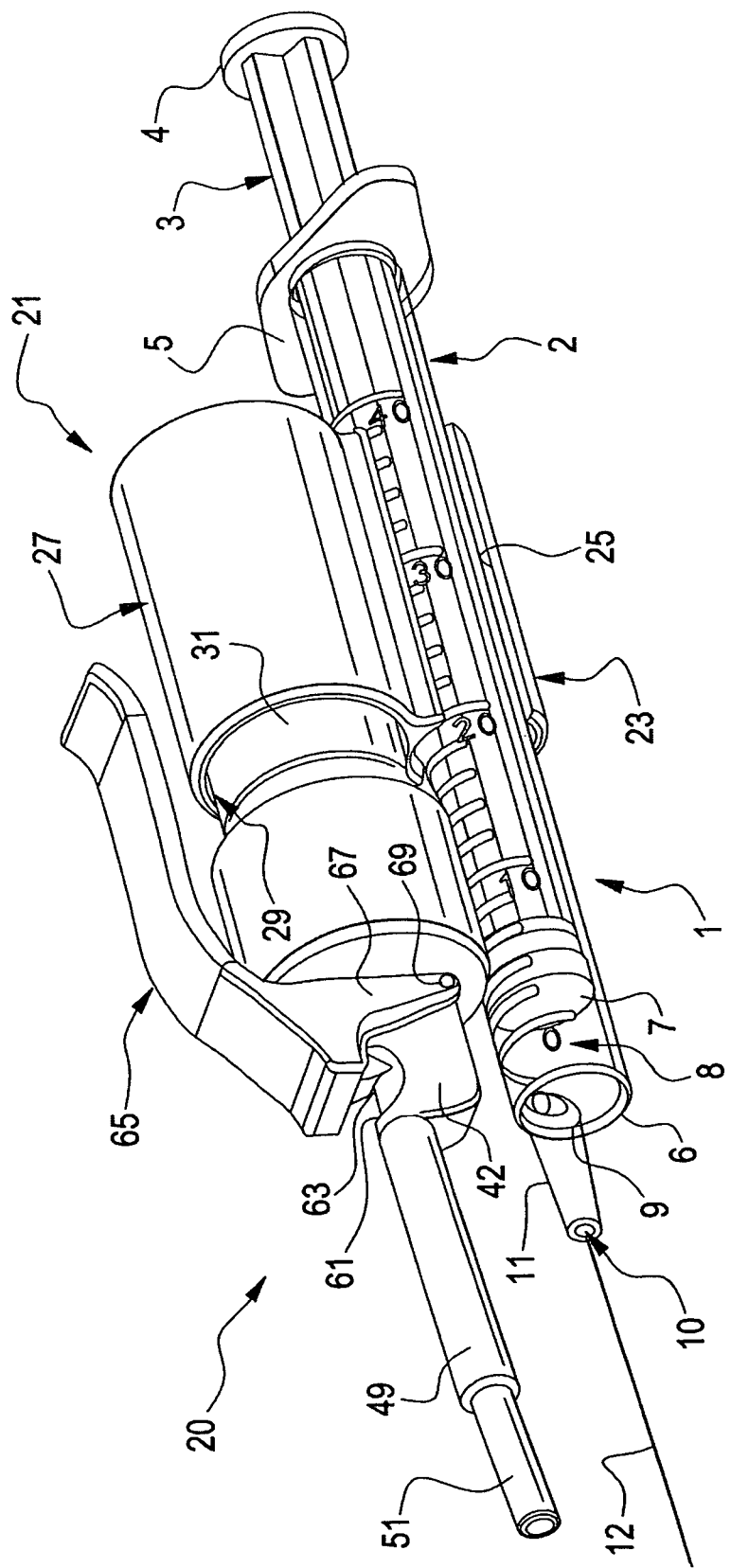
FIG. 1 shows a side perspective view of a first embodiment of the present invention as attached to a disposable syringe.
Figure 2:
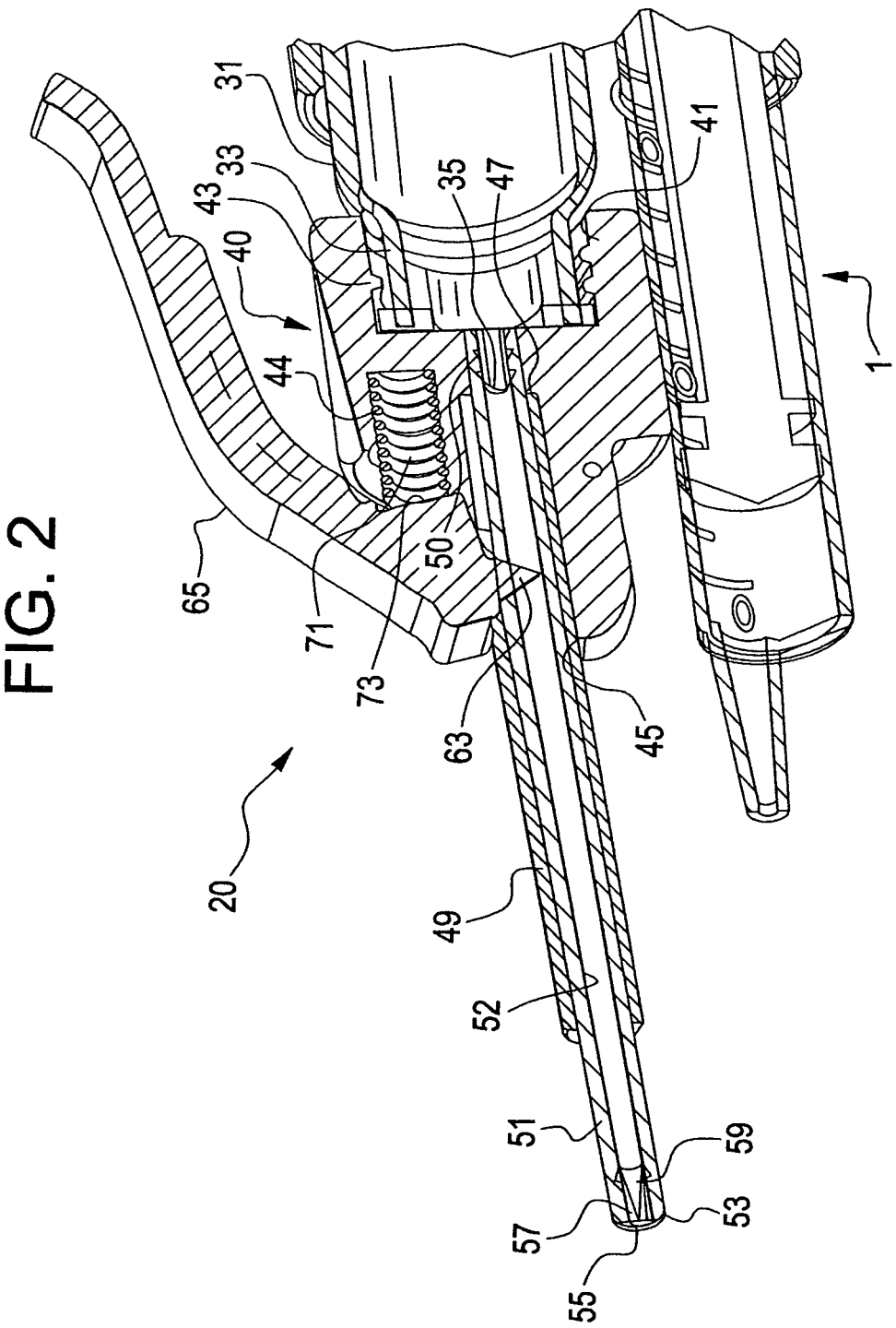
FIG. 2 shows an enlarged side perspective view of the first embodiment of the present invention from a similar perspective as that of FIG. 1, but with certain parts broken away to show details and other parts shown in cross-section to show details.

FIGS. 1-2 show a first embodiment of the present invention. Reference is first made to FIG. 1. As shown, a syringe 1 includes an elongated barrel 2 that is typically cylindrical in outer configuration, a plunger 3 having a proximal pad 4 that is engaged by a finger of the user, and a perpendicular tab 5 on the barrel 2 of the syringe 1 that is grasped by other fingers of the user while the pad 4 is being pushed to cause the plunger 3 to move in the distal direction toward the end 6 of the barrel 2.

The plunger 3 includes a piston 7 that pushes liquid in the chamber 8 through the outlet 9 in the chamber 8. A needle 12 is inserted into the opening 10 formed downstream of the outlet 9 in a tapered port 11. As is well known, the needle is thin and hollow permitting the medicament within the chamber 8 to be dispensed therethrough. The needle can be of any length so long as its distal end extends beyond the end of the tube 51 described below.

With reference to FIGS. 1 and 2, the first embodiment of the present invention is generally designated by the reference numeral 20. The inventive dispenser 20 includes attachment means comprising a clip 21 having a clip portion 23 of arcuate construction and having a longitudinally elongated slot 25 having a width slightly smaller than the diameter of the barrel 2 of the syringe 1. The clip portion 23 is made of a flexible resilient material so that the width of the slot 25 may be temporarily enlarged by flexing it open, whereupon the barrel 2 of the syringe 1 may be inserted within the clip portion 23 and the flexing may be reversed causing the clip portion 23 to resiliently engage the outer periphery of the barrel 2 to retain the clip portion 23 assembled thereon.

The clip portion 23 also includes a receptacle or receptacle portion 27 including an internal chamber 29 defined by a closed end wall and a distal opening and is sized to receive a canister 31 pre-filled with a topical anesthetic. The internal walls of the chamber 29 are sized and configured to snugly receive the canister 31 while it being easy to remove the canister 31 when it is desired to replace or replenish it. If desired, the internal walls of the chamber 29 may be roughened or provided with a lining such as of rubber or other sticky material to enhance the holding power of the chamber 29 for the canister 31.

As best seen in FIG. 2, the canister 31 includes a distal neck portion 33 having an outlet 35 that is initially closed, for example, by a piercable disc (not shown) that may suitably be pierced to allow the topical anesthetic contained within the canister 31 to be dispensed.

With more particular reference to FIG. 2, the dispenser 20 also includes a housing 40 including a threaded recess 41. Preferably, the neck portion 33 of the canister 31 has external threads and meshing with the threads 43 within the opening 41 to allow the canister 31 to be releasably suitably fastened to the housing 40. The housing 40 includes a stepped cylindrical bore 45 with the step occurring at a shoulder 47. The distal portion of the bore 45 has an enlarged diameter and is sized to receive a rigid tube 49 which engages the shoulder 47 in assembled relation. The tube 49 may be secured to the housing 40 in any suitable manner such as through the use of an interference fit or adhesive. A flexible tube 51 is inserted into the rigid tube 49 and extends into the smaller diameter portion of the bore 45 as best seen in FIG. 2, surrounding the distal outlet 35 of the canister 31.

The tube 51 has a distal end 53 having an opening 55 that may, if desired, be defined by a nozzle insert 57 inserted into the opening 55 and having a particularly configured passageway 59 to cause topical anesthetic sprayed therefrom to spray in a desired pattern. The distal end of the tube 51 is flexible and may be bent by a physician into a desired angulation so that the topical anesthetic is sprayed in a desired location with respect to the location where the syringe needle will be inserted beneath the skin of the patient. The needle 12 extends beyond the distal termination of the tube 51 so that the tube 51 doesn't interfere with insertion of the needle subcutaneously. The tube 51 has a proximal end 52 (FIG. 2) receiving the outlet 35 of the canister 31.

The rigid tube 49 has an opening 61 (reference numeral shown in FIG. 1) through which a tube compressor 63 protrudes. As best seen in FIG. 1, the tube compressor 63 has an arcuate distal portion engaging the outer surface of the flexible tube 51 and is able to compress the tube 51 at that location to completely occlude the passageway 52 extending within the tube 51.

Valve means comprising a tube compressor 63 is integrally formed with a lever 65 pivotably mounted on the dispenser 40, the tube compressor 63 including an integrally formed arcuate shoulder (FIG. 1). In this regard, reference is made to FIG. 1 which shows the depending portion 67 of the lever 65 receiving a pin 69 extending through openings in the lever 65 (not shown) and an opening (not shown) through a portion 42 of the dispenser 40 so that the lever 65 pivots about the pin 69.

With reference to FIG. 2, the housing 40 includes a recess 44 that receives biasing means comprising a spring 71. The spring 71 has a proximal end engaging a proximal shoulder of the recess or blind bore 44 and a distal end engaging a shoulder 73 of the lever 65 so that the action of the compression spring 71 causes a force to be imposed in the left-hand direction in the view of FIG. 2 to cause the lever 65 to tend to pivot in a counterclockwise direction in the view of FIG. 2 about the pin 69 (FIG. 1). In this way, the tube compressor 63 is biased to the position shown in FIG. 2 at which it completely compresses the flexible tube 51 and completely occludes the passageway 52 to preclude any topical anesthetic from the canister 61 from passing through the nozzle 57.

If desired, the proximal end of the flexible tube 51 may be provided with a hollow piercing element (not shown) designed to pierce a disc (not shown) on the distal outlet 35 of the canister 31 when the canister 31 neck 33 is being screwed into the threaded opening 41 of the dispenser 40 to open access to the canister contents. In this way, once the canister 31 is so installed, with the lever 65 biased to the position shown in FIG. 2, the anesthetic is ready to be dispensed, but will not be dispensed until the lever 65 is pivoted in the clockwise direction in the view of FIG. 2 to permit the tube compressor 63 to relieve pressure on the outer periphery of the flexible tube 51 and facilitate flow of anesthetic through the passageway 52 and out the nozzle 57 via the nozzle passageway 59.

With the first embodiment of the present invention having been described in great detail hereinabove, its method of operation will now be explained. First, a syringe 1 is chosen and a desired needle 12 is installed into the port 10 thereof so that its distal end is distal of the nozzle 59 of the tube 51. The inventive dispenser 20 is attached to the barrel 2 of the syringe by expanding the longitudinal slot 25 in the clip portion 23, inserting the barrel 2 therewithin, and releasing the clip portion 23 to cause its inner surfaces to squeeze against the barrel 2 to retain it in appropriate position. In that position, the clip portion 23 may be slid along the barrel 2 to assume any desired location along the barrel length.

The location on the skin of the patient where an injection is to take place is determined and the syringe 1 with the dispenser 20 attached thereto is positioned at a desired location and angle of skin penetration approximately 1 to 2 centimeters above the skin. The lever 65 is depressed to pivot it about the pivot pin 69 to release the tube compressor 63 from the outer periphery of the flexible tube 51 to permit flow of the topical anesthetic such as ethyl chloride for a period of time, such as 1 to 3 seconds.

Either while the topical anesthetic is flowing or just after the flow of the topical anesthetic is stopped, the skin is then penetrated by the needle of the syringe 1 to a desired depth and, once the intramuscular location has been verified, the medicament is injected to the desired depth and amount. Injections may be subcutaneous, intramuscular or intradermal.

If desired, the needle may be retracted a desired distance with additional injection occurring or may be removed so that the next location can be chosen. During the process of injection including multiple injections at the same site of needle penetration, additional topical anesthetic may be dispensed as desired to maintain the numbness of the skin at that location.

If during the process of injection, the canister 31 runs out of topical anesthetic, it may be removed from the receptacle 29 and replaced with a replacement canister. The canister 31 may also be refillable.

When the injection process is completed, the syringe 1 may be removed from the clip portion 23 and suitably discarded and the dispenser 20 may be re-used with other syringes.

As such, in this way, the present invention provides an effective way of dispensing a topical anesthetic such as ethyl chloride onto the skin of a patient where an injection is to take place so that the injection is painless. The present invention is not limited for use in association with injections in the face for aesthetic enhancement. Rather, it may be used as attached to any syringe or other injection device used to inject any medication for any purpose. For example, the inventive device may be used with injection devices associated with diabetes glucose monitors and multiple needle allergy introducers.

In the first embodiment of the present invention, the clip 27 is made of any suitable material such as molded plastic or light metal, although molded plastic is preferred. The housing 40 may be made of a molded plastic as may the lever 65 with its integral tube compressor 63. The tube 49 is made of any suitable rigid plastic while the tube 51 is made of any suitable flexible material allowing the distal end thereof to be bent to a desired angulation and to retain its bent orientation.

Figure 3:
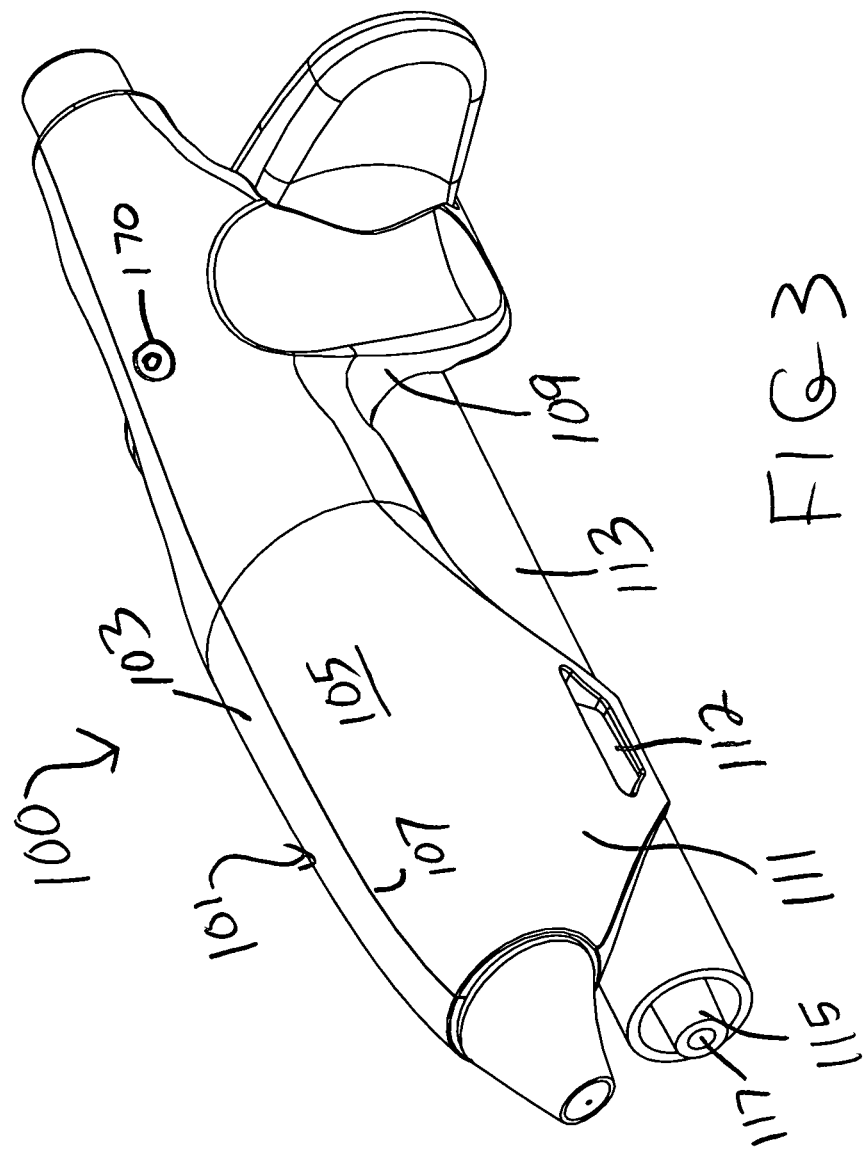
FIG. 3 shows a perspective view of a second embodiment of the present invention.
Figure 4:
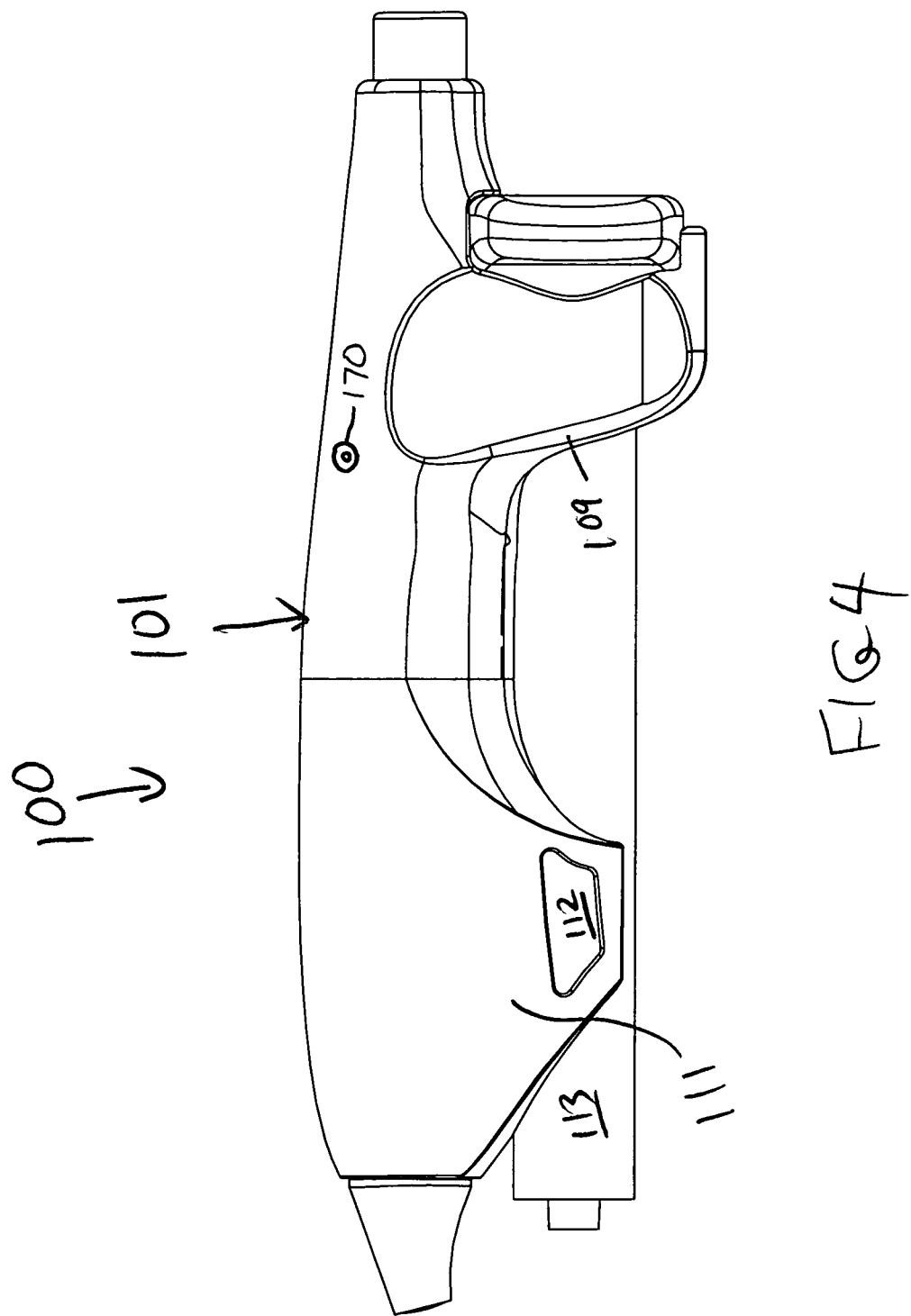
FIG. 4 shows a side view of the second embodiment of the present invention.

With reference, now, to FIGS. 3-9, a second embodiment of the present invention is generally designated by the reference numeral 100 and is seen to be made up of an elongated housing 101 including two housing halves 103 and 105 interconnected together at the location of two splits of which one of the splits 107 is seen in FIGS. 3, 6 and 9, in particular, and of which the other split is diametrically opposite.

As seen in FIG. 3, the housing 101 includes a first clip 109 at the proximal end of the housing and a second clip 111 at the distal end of the housing. The barrel 113 of a syringe is seen releasably received within the clips 109 and 111. As understood from the details of the syringe 1 described in conjunction with the first embodiment of the present invention, the end 115 of the syringe includes an opening 117 to which is installed a desired needle and the proximal end of the barrel 113 includes an opening 119 (FIG. 7) leading to a passageway 121 that receives a plunger such as the plunger 3 illustrated in FIG. 1. The typical syringe barrel 113 includes a series of gradations on its outer surface that allow one to determine the volume of fluid contained within the chamber 121. In order to view these gradations, the clip 111 includes opposed trapezoidal windows 112 best seen in FIGS. 3, 4 and 5.

With particular reference to FIG. 7, the housing 101 includes an internal chamber 123 that receives a canister 125 of a topical anesthetic. The canister 125 includes an internal chamber 127 that receives the topical anesthetic and includes a valve 129 activated by moving the elongated actuator 131 to the right in the view of FIG. 7 (or the canister 125 to the left with respect to the fixed actuator 131) in a manner well understood by those of ordinary skill in the art. The actuator 131 includes an elongated passageway 133 interconnected to the chamber 127 via the valve 129. A spring 135 is interposed between the actuator 131 and the wall 137 defining a part of the housing containing the valve 129. In this way, when the actuator 131 is moved to the right in the view of FIG. 7 with respect to the canister 125 (or vice versa), once the force moving the actuator 131 is relieved, the spring 135 moves the actuator 131 back to the configuration shown in FIG. 7. In one variation, the canister 125 is not refillable. As such, when it is depleted of topical anesthetic, the device 100 must be discarded. In another variation, with reference to FIGS. 3, 4, 6 and 7, a fill port 170 may be provided and connected to the chamber 127 by conduit 172 (FIG. 7). The canister may be refilled through the fill port 170 and conduit 172 in a manner well understood. The fill port 170 is sealed when not in use, for example, as is an inflation valve on an athletic ball.

With further reference to FIG. 7, it should be understood that actuation of the valve 129 is equally possible by fixing the position of the actuator 131 and moving the canister 125 to the left in the view of FIG. 7 with respect thereto. In fact, this is the preferred manner of opening of the valve 129 to cause release of the topical anesthetic from the chamber 127 of the canister 125.

For this purpose, with further reference to FIG. 7, a button 140 is provided at the right hand side of the housing 101 in the view of FIG. 7 and is coupled to an elongated stem 141 having a distal end 143 engaging the closed wall 128 of the canister 125. Thus, when the button 140 is pushed to the left in the view of FIG. 7, the integral stem 141 moves the canister 125 to the left in the view of FIG. 7. The housing 101 also has mounted thereon a nozzle 150 that includes an elongated passageway 151 aligned with the passageway 133 through the canister actuator 131. The bore 151 is connected to a nozzle bore 153 at the distal end 152 of the nozzle 150 and topical anesthetic dispensed from the chamber 127 exits the inventive device 100 via the nozzle bore 153.

The nozzle 150 is fixed into the housing 101 by virtue of an annular groove 155 that receives the inwardly directed edge or annular shoulder 102 of the distal end of the housing 101. This is possible since, as explained above, the housing 101 comprises two housing halves 103 and 105 that cause the housing to be longitudinally split. The two housing halves 103 and 105 combine together to provide an annular shoulder 102 that engages in the groove 155 to retain the nozzle 150 in fixed mount within the housing 101. The needle (not shown) of the associated syringe extends distally of the nozzle bore 153 in the same manner as shown in FIG. 1.

The fixed relationship between the nozzle 150 and the housing 101 means that when the button 140 is depressed to the left in the view of FIG. 7, the nozzle 150 is constrained from movement with respect to the housing 101. Thus, with the actuator 131 received within a bore 157 of the nozzle 150, the actuator 131 is also constrained from longitudinal movement. Thus, when the button 140 is depressed to the left in the view of FIG. 7, the cannister 125 moves with respect to the actuator 131 to open the valve 129 and cause dispensing of the topical anesthetic from the chamber 127 through the valve 129 through the bore 133 and thence through the bore 151 and the nozzle bore 153 onto the desired location on the patient. As is understood by those skilled in the art, the bore 133 is fluidly connected to the chamber of the valve 129 and to the chamber 127 in a manner well known. When the button 140 is released, the spring 135 moves the cannister 125 to the right along with the stem 143 and button 141, restoring them to the position shown in FIG. 7. If desired, a cam device (not shown) may be associated with the actuator button 140 so that a prescribed metered dose of topical anesthetic is dispensed each time the button 140 is pushed, regardless of how long it is held in the depressed position. Such cam devices are generally known.

Figure 5:
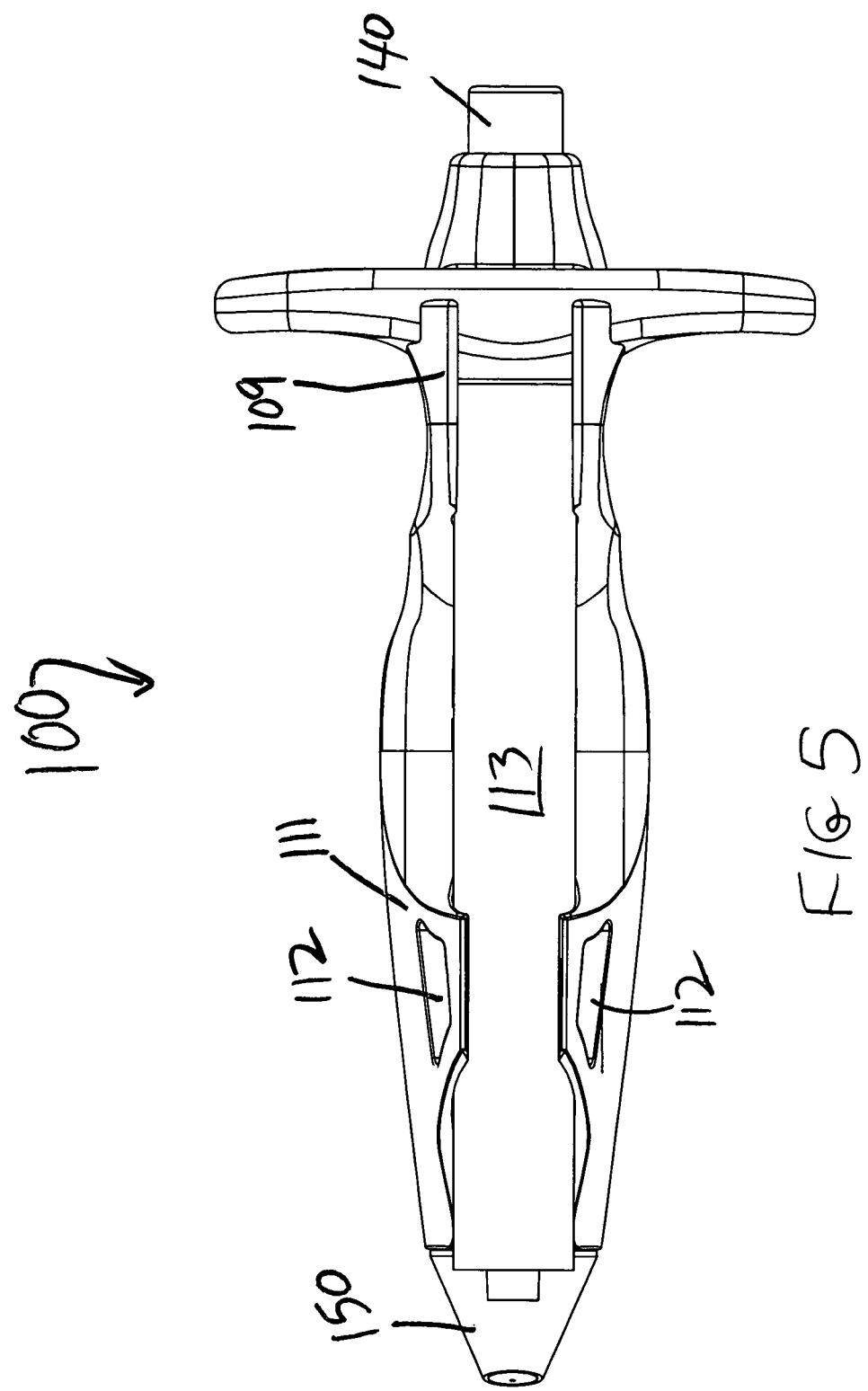
FIG. 5 shows a bottom view of the second embodiment of the present invention.

With particular reference to FIGS. 5 and 6, it is seen that two wing-like appendages 160 and 162 extend in opposite directions close to the proximal end of the housing 101. These appendages include respective distally facing arcuate surfaces 161 and 163. Additional arcuate surfaces 165 and 167 are located on opposed sides of the housing 101 (FIG. 6, in particular). The purpose for the appendages 160 and 162 with their arcuate surfaces 161 and 163, respectively, and the arcuate surfaces 165 and 167 on the housing 101 is to receive fingers of the user on either side of the housing 101 to facilitate secure gripping of the device 100, whereupon the thumb may be used to depress the button 140 to dispense the topical anesthetic.

In the assembly of the inventive device 100, with the housing halves 103 and 105 separated, the nozzle 150 is assembled to the canister 125 with the actuator 131 received within the bore 157 of the nozzle. As assembled, these devices are placed into one housing half in the manner shown in FIG. 7, and the button 140 with its actuator stem 141 is inserted laterally with the distal end 143 of the stem 141 engaging the wall 128 of the canister 125. Ribs 134, 136 and 138, among others, align the canister 125 in the position shown in FIG. 7, while the interaction between the groove 155 and the wall 102 of the housing 101 aligns the nozzle 150 in the desired location. Similarly, ribs 162 and 164 suitably align the actuator stem 141 in the position shown in FIG. 7.

The housing halves are then assembled together using a suitable adhesive and perhaps an ultraviolet activated adhesive to seal the housing halves 103 and 105 together with the nozzle 150, canister 125, button 140, and stem 141 in assembled relation as shown in FIG. 7.

In the preferred manner of use of the second embodiment 100, it is completely disposable. That is, the canister 125 is not replaceable due to the hermetic sealing of the housing 101. Thus, when the canister 125 is empty, the entire device 100 is discarded. Alternatively, as explained above, the fill port 170 and conduit 172 permit replenishment of the canister 125.

Operation of the second embodiment in conjunction with use of a syringe is the same as explained with regard to the first embodiment.

The housing 101 is preferably made of plastic by any desired method including injection molding.

As such, an invention has been disclosed in terms of preferred embodiments thereof which fulfill each and every one of the objects of the invention as set forth hereinabove, and provide a new and useful syringe-attached topical anesthetic dispenser of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:
1. A topical anesthetic dispenser, comprising:
a) a housing having a chamber sized to removably receive a cannister containing liquid anesthetic;

b) attachment means on said housing for releasably attaching said housing to a syringe for injecting a medicament into a patient's skin;
c) said cannister having an outlet for dispensing said anesthetic;
d) said housing including a spray nozzle outlet fluidly connected to said outlet of said cannister and said spray nozzle outlet comprising a spray nozzle through which said anesthetic is topically sprayed onto a surface of the patient's skin when dispensed from said cannister; and
e) valve means for selectively controlling flow of said anesthetic from said cannister to said spray nozzle, said valve means comprising a valve incorporated into said cannister and further including a valve actuator comprising an elongated reciprocable hollow tube mounted on said cannister and having a proximal end adjacent a valve chamber, and a distal end extending distally of said cannister and fixed to said housing, said tube having a passageway therethrough connected to said spray nozzle; said valve actuator further including an actuator button on a proximal end of said housing, whereby when said actuator button is moved distally, said cannister is moved distally with respect to said elongated hollow tube to cause said valve means to open, said valve including a spring biasing said cannister proximally with respect to said tube, whereby when said actuator button is released, said cannister moves proximally to close said valve.

2. The dispenser of claim 1, wherein said attachment means comprises a clip adapted to releasably attach around a barrel of said syringe.

3. The dispenser of claim 2, wherein said clip includes an arcuate wall and a longitudinally extending split.

4. The dispenser of claim 2, wherein said clip comprises a pair of longitudinally spaced clips adapted to releasably attach around said barrel of said syringe.

5. The dispenser of claim 4, wherein said syringe includes a needle having a distal tip, said distal tip being distal of said spray nozzle.

6. The dispenser of claim 1, wherein said valve means comprises an aerosol valve, and said cannister being refillable.

7. A topical anesthetic dispenser, comprising:
a) a housing having a chamber sized to removably receive a cannister of liquid anesthetic;
b) a pair of clips on said housing for releasably attaching said housing to a syringe for injecting a medicament into a patient's skin;
c) said cannister having an outlet for dispensing said anesthetic;
d) said housing including a spray nozzle outlet fluidly connected to said outlet of said cannister and said spray nozzle outlet comprising a spray nozzle through which said anesthetic is topically sprayed onto a surface of the patient's skin when dispensed from said cannister;
e) valve means for selectively controlling flow of said anesthetic from said cannister to said spray nozzle; and
f) an actuator for actuating said valve means comprising a button which when pushed moves the cannister with respect to said valve means to open said valve means, and a spring biasing said valve means toward a closed position thereof, said spring moving said cannister with respect to said valve means when said button is released to close said valve means.

8. The dispenser of claim 7, wherein each clip of said pair of clips includes an arcuate wall and a longitudinally extending split.

9. The dispenser of claim 7, wherein said housing is generally cylindrical and said actuator is located at a proximal end of said housing for actuating said valve means.

10. The dispenser of claim 7, wherein said actuator further includes an elongated reciprocable hollow tube mounted on said cannister and having a proximal end adjacent a valve chamber, and a distal end extending distally of said cannister, said tube having a passageway therethrough connected to said spray nozzle.

11. The dispenser of claim 7, wherein said housing is made of plastic.

12. A topical anesthetic dispenser, comprising:
a) a receptacle sized to removably receive a cannister of liquid anesthetic;
b) attachment means on said receptacle for releasably attaching said receptacle to a syringe for injecting a medicament into a patient's skin, said syringe having a barrel defining a chamber receiving a plunger, said attachment means comprising a clip releasably attachable around said barrel;
c) said cannister having an outlet for dispensing said liquid anesthetic;
d) a passageway fluidly connected to said outlet of said cannister at a proximal end of said passageway, and said passageway having a distal end comprising a spray nozzle through which said anesthetic is topically sprayed onto a surface of the patient's skin when dispensed from said cannister; and
e) valve means for selectively controlling flow of said anesthetic from said cannister to said spray nozzle, said valve means comprising a valve within said cannister which is biased by a spring to a closed position thereof, said cannister being movable against a force of said spring and with respect to said passageway to open said valve, said cannister being movable by said spring to close said valve.

\* \* \* \* \*